(12) United States Patent
Bailly et al.

(10) Patent No.: US 8,748,636 B2
(45) Date of Patent: Jun. 10, 2014

(54) PROCESS FOR PREPARING BENZOFURAN DERIVATIVES SUBSTITUTED AT POSITION 5

(71) Applicant: Sanofi, Paris (FR)

(72) Inventors: Frederic Bailly, Paris (FR); Xavier Bon, Paris (FR); Philippe Vayron, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/742,810

(22) Filed: Jan. 16, 2013

(65) Prior Publication Data

US 2013/0165674 A1 Jun. 27, 2013

Related U.S. Application Data

(63) Continuation of application No. PCT/FR2011/051751, filed on Jul. 20, 2011.

(30) Foreign Application Priority Data

Jul. 21, 2010 (FR) ...................................... 10 55951

(51) Int. Cl.
C07D 307/85 (2006.01)

(52) U.S. Cl.
USPC ........................................................ 549/468

(58) Field of Classification Search
USPC ........................................................ 549/468
See application file for complete search history.

(56) References Cited

U.S. PATENT DOCUMENTS

| | | | |
|---|---|---|---|
| 3,937,737 A | 2/1976 | Eiglmeier | |
| 5,223,510 A | 6/1993 | Gubin et al. | |
| 6,828,448 B2 | 12/2004 | Fino et al. | |
| 6,846,936 B2 | 1/2005 | Biard | |
| 6,949,583 B2 | 9/2005 | Assens et al. | |
| 7,148,240 B2 | 12/2006 | Assens et al. | |
| 2012/0065411 A1 | 3/2012 | Kretzschmar et al. | |
| 2012/0077995 A1 | 3/2012 | Kretzschmar et al. | |
| 2012/0289717 A1 | 11/2012 | Friesz et al. | |
| 2012/0330036 A1 | 12/2012 | Friesz et al. | |
| 2013/0012729 A1 | 1/2013 | Bailly et al. | |

FOREIGN PATENT DOCUMENTS

| | | |
|---|---|---|
| EP | 0471609 | 2/1992 |
| EP | 0735083 | 10/1996 |
| EP | 1315709 B1 | 6/2003 |
| FR | 2238696 | 2/1975 |
| WO | WO 02/16340 | 2/2002 |
| WO | WO 2005/012301 | 2/2005 |
| WO | WO 2009/044143 | 4/2009 |
| WO | WO 2010/038029 | 4/2010 |
| WO | WO 2010/040261 | 4/2010 |
| WO | WO 2011/107705 | 9/2011 |
| WO | WO 2012/010788 | 1/2012 |
| WO | WO 2012/127173 | 9/2012 |
| WO | WO 2012/131408 | 10/2012 |
| WO | WO 2012/131409 | 10/2012 |
| WO | WO 2012/131410 | 10/2012 |

OTHER PUBLICATIONS

U.S. Appl. No. 13/638,484, filed Aug. 30, 2012, Bailly, et al.
U.S. Appl. No. 13/638,500, filed Sep. 28, 2012, Priem, et al.
U.S. Appl. No. 13/628,867, filed Sep. 27, 2012, Bon, et al.
U.S. Appl. No. 13/711,891, filed Dec. 12, 2012, Friesz.
U.S. Appl. No. 13/740,505, filed Jan. 14, 2013, Friesz, et al.
International Search Report for WO2012/010802 dated Jan. 26, 2012.
Haddadin, et al., Reaction of Benzofurazan Oxide With Unsymmetrical 1,3-Diketones: Steric Polar Effects, Tetrahedron, vol. 32, (1976), pp. 719-724.
U.S. Appl. No. 13/599,374—Non-Final Office Action dated Apr. 23, 2013.
U.S. Appl. No. 13/599,374—Response to Non-Final Office Action filed Jul. 23, 2013.

*Primary Examiner* — Andrew D Kosar
*Assistant Examiner* — Raymond Covington
(74) *Attorney, Agent, or Firm* — Scully, Scott, Murphy & Presser, P.C.

(57) ABSTRACT

The disclosure relates to a process for preparing benzofuran derivatives of general formula I:

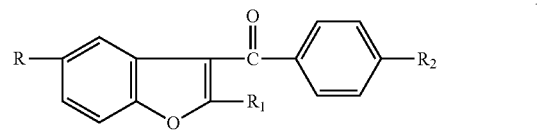

in which R, $R_1$, and $R_2$ are as defined in the disclosure; by coupling the hydroxylamine with a diketone of general formula III:

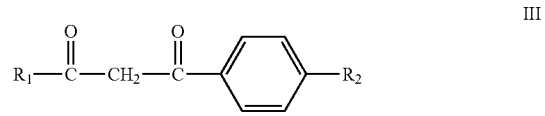

in order to form an oxime that is then cyclized by heating in order to form the desired compound.

22 Claims, No Drawings

PROCESS FOR PREPARING BENZOFURAN DERIVATIVES SUBSTITUTED AT POSITION 5

This application is a continuation of International Application No. PCT/FR2011/051751, filed Jul. 20, 2011, which is incorporated herein by reference in its entirety; which claims the benefit of priority of French Patent Application No. 1055951, filed Jul. 21, 2010.

The present invention relates generally to the preparation of benzofuran derivatives substituted at position 5.

The invention relates to a process for preparing benzofuran derivatives substituted at position 5 of general formula:

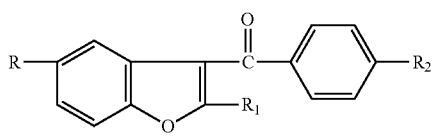

in which R represents a nitro or ester group —COOR' in which R' represents a hydrogen atom or an alkyl group, $R_1$ represents hydrogen or an alkyl group and $R_2$ represents hydrogen, a halogen or a hydroxyl, haloalkyl, alkyl, alkoxy, dialkylaminoalkoxy or dialkylaminoalkyl group.

More specifically, the invention relates to a process for preparing compounds of formula (I) in which R represents a nitro group, these compounds of formula (I) being known as 5-nitrobenzofuran derivatives of general formula I':

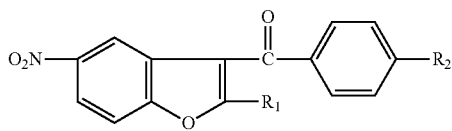

in which R represents a nitro group, $R_1$ represents hydrogen or an alkyl group and $R_2$ represents hydrogen, a halogen or an alkyl, alkoxy or dialkylaminoalkoxy group.

More specifically, the invention relates to a process for preparing compounds of formula (I) in which R represents an ester group —COOR', these compounds of formula (I) being known as benzofuran derivatives substituted at position 5 of general formula I":

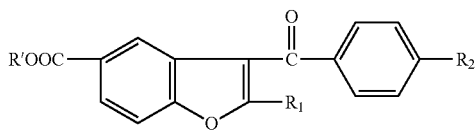

in which R represents an ester group —COOR' in which R' represents a hydrogen atom or an alkyl group, $R_1$ represents an alkyl group and $R_2$ represents hydrogen or a hydroxyl, haloalkyl, dialkylaminoalkoxy or dialkylaminoalkyl group.

In formulae I, I' and I" above:
$R_1$ in particular represents a linear or branched $C_1$-$C_8$ alkyl group, especially a linear or branched $C_1$-$C_4$ alkyl group, such as methyl, ethyl, n-propyl, isopropyl, n-butyl, sec-butyl or tert-butyl, or alternatively a substituted or unsubstituted phenyl group, $R_2$ in particular represents a chlorine, bromine or iodine or a linear or branched $C_1$-$C_8$ alkyl group, especially a linear or branched $C_1$-$C_4$ alkyl group such as methyl, ethyl, n-propyl, isopropyl, n-butyl, sec-butyl or tert-butyl; a linear or branched $C_1$-$C_8$ alkoxy group, especially a linear or branched $C_1$-$C_4$ alkoxy group such as methoxy, ethoxy, n-propoxy, isopropoxy, n-butoxy, sec-butoxy or tert-butoxy; or a dialkylaminoalkyl group or alternatively a dialkylaminoalkoxy group in which each linear or branched alkyl group is of $C_1$-$C_8$ and the linear or branched alkoxy group is of $C_1$-$C_8$, especially in which each linear or branched alkyl group is of $C_1$-$C_4$ such as methyl, ethyl, n-propyl, isopropyl, n-butyl, sec-butyl or tert-butyl and the linear or branched alkoxy group is of $C_1$-$C_4$ such as methoxy, ethoxy, n-propoxy, isopropoxy, n-butoxy, sec-butoxy or tert-butoxy, R' is a linear or branched $C_1$-$C_4$ alkyl group such as isopropyl.

According to one embodiment, $R_1$ represents n-butyl and $R_2$ represents 3-(di-n-butylamino)propoxy.

According to one embodiment, $R_1$ represents n-butyl and $R_2$ represents 3-(di-n-butylamino)propyl.

The compounds of formula I above and more specifically those of formula I' are, for the majority, compounds described in patent EP 0 471 609 where they are presented as intermediate products for the preparation of aminoalkoxybenzoylbenzofuran derivatives that are useful for their therapeutic applications in the cardiovascular field.

Among these aminoalkoxybenzoylbenzofuran derivatives, 2-n-butyl-3-{4-[3-(di-n-butylamino)propoxy]benzoyl}-5-methanesulfonamidobenzofuran, commonly known as dronedarone, and also pharmaceutically acceptable salts thereof, has proven to be particularly advantageous especially as an antiarrhythmic agent.

Patent application WO 2009/044 143 and patent EP 0 471 609 disclose various process steps which, when combined, make it possible, starting with 4-hydroxyacetophenone, to gain access to 2-n-butyl-3-{4-[3-(di-n-butylamino)propoxy]benzoyl}-5-nitrobenzofuran (referred to hereinbelow as Compound A), which is an intermediate that is particularly advantageous for preparing dronedarone. According to this process, the reaction sequence below may be envisioned:

a) coupling 4-hydroxyacetophenone with ethyl valerate in the presence of an alkali metal alkoxide (yield: 65%), b) cyclization of the 1-(4-hydroxyphenyl)-1,3-heptanedione thus obtained with O-(4-nitrophenyl)hydroxylamine to form 2-n-butyl-3-(4-hydroxybenzoyl)-5-nitrobenzofuran (yield: 69%). These steps are described in patent application WO 2009/044143, c) etherification of the 5-nitrobenzofuran derivative thus formed with 1-chloro-3-(di-n-butylamino)propane to form compound A (yield: 88.76%).

This step is described in patent EP 0 471 609.

Consequently, Compound A could not be obtained in an overall yield of greater than 39% starting with 4-hydroxyacetophenone and according to the combination of steps reported above.

The search for a preparation process capable of providing Compound A starting with 4-hydroxyacetophenone and in overall yields that are significantly higher than those provided in the prior art consequently remains of unquestionable interest.

It has now been found that Compound A can be synthesized in overall yields of at least 56% starting with 4-hydroxyacetophenone by means of the combination of steps using 1-{4-[3-(di-n-butylamino)propoxy]phenyl}-1,3-heptanedione rather than 1-(4-hydroxyphenyl)-1,3-heptanedione.

The compounds of formula I above and more specifically those of formula I″ are, for the majority, compounds described in patent EP 1 315 709 where they are presented as intermediate products for the final preparation of aminoalkylbenzoylbenzofuran derivatives that are useful for their therapeutic applications in the cardiovascular field.

Among these aminoalkylbenzoylbenzofuran derivatives, isopropyl 2-butyl-3-{4-[3-(dibutylamino)propyl]benzoyl}-1-benzofuran-5-carboxylate, commonly known as celivarone, and also the pharmaceutically acceptable salts thereof, has proven to be particularly advantageous especially as an antiarrhythmic agent.

Contrary to the synthetic route described in patent EP 1 315 709, this synthetic route is convergent and makes it possible to reduce the number of steps. This route thus constitutes an economically viable alternative. This route makes it possible especially to avoid a Sonogashira-type organometallic coupling step which uses expensive reagents and a Friedel-Crafts step which generates large amounts of aluminum salts.

According to the invention, the benzofuran derivatives substituted at position 5 of formula I may be prepared by coupling, in the presence of an acid, the hydroxylamine of formula II:

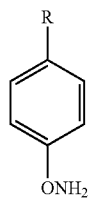

in which R represents a nitro or ester group —COOR′, R′ having the same meaning as previously, with a diketone of general formula III:

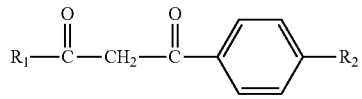

in which $R_1$ and $R_2$ have the same meaning as previously, to form an oxime of general formula:

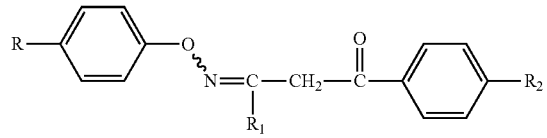

in the form of a mixture of E and Z isomers, in which $R_1$ and $R_2$ have the same meaning as previously, and this oxime is cyclized by heating to form the desired compound.

According to one embodiment of the invention, the 5-nitrobenzofuran derivatives of formula I′ may be prepared by coupling, in the presence of an acid, O-(4-nitrophenyl)hydroxylamine of formula II′, this compound corresponding to the compound of formula II in which R represents —NO₂:

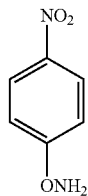

with a diketone of general formula III:

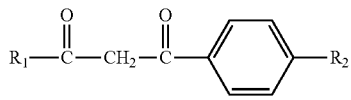

in which $R_1$ and $R_2$ have the same meaning as previously, to form an oxime of general formula:

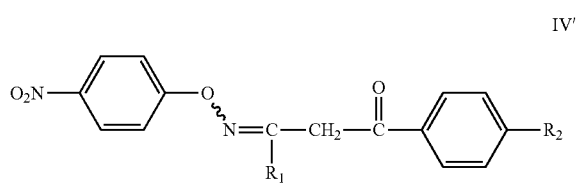

in the form of a mixture of E and Z isomers, in which $R_1$ and $R_2$ have the same meaning as previously, and this oxime is cyclized by heating to form the desired compound; the compound of formula IV′ corresponding to the compound of formula IV′ in which R represents —NO₂.

According to one embodiment of the invention, the benzofuran derivatives of formula I″ may be prepared by coupling, in the presence of an acid, the compound of formula II″, this compound corresponding to the compound of formula II in which R represents —COOR′, R′ being as defined previously:

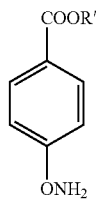

with a diketone of general formula III:

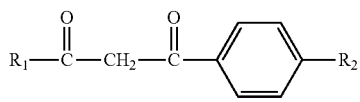

in which $R_1$ and $R_2$ have the same meaning as previously, to form an oxime of general formula:

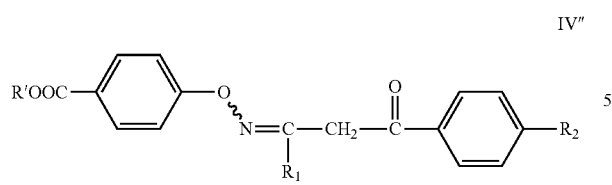

IV″ in the form of a mixture of E and Z isomers, in which $R_1$ and $R_2$ have the same meaning as previously, and this oxime is cyclized by heating to form the desired compound; the compound of formula IV' corresponding to the compound of formula IV in which R represents —COOR', R″ being as defined previously.

According to one embodiment, the oxime is reacted to form a salt such as the hydrochloride.

Usually, the coupling is performed in the presence of an acid, preferably a weak acid, optionally combined with a strong acid, generally an organic or mineral acid such as a hydracid, for example hydrochloric acid. This acid or this mixture of acids may be combined, where appropriate, with an organic or mineral solvent, for example N,N-dimethylformamide, dimethyl sulfoxide, an ether such as tetrahydrofuran, diethyl ether or dioxane, or alternatively an alcohol such as methanol or ethanol. However, according to a preferred embodiment, the coupling proceeds solely in an acidic medium which serves both as reagent and as solvent.

The weak acid in question is generally chosen from acids whose boiling point is less than 150° C., for example formic acid or, preferably, acetic acid. In addition, this weak acid may be used in solution, for example in water or in an organic or mineral solvent or, preferably, alone. By way of example, when this weak acid is acetic acid, it preferably corresponds to glacial acetic acid.

The coupling reaction usually proceeds at room temperature to form the oxime of formula IV. This oxime is then cyclized by in situ heating, i.e. in the same medium in which it is formed. In another manner, the cyclization of this oxime may be performed ex situ, i.e. separately from the medium in which it is formed, and in a solvent such as, for example, the solvent used during this formation.

Usually, the process of the invention proceeds at a temperature ranging from room temperature up to about 150° C. In general, this process is undertaken at room temperature when the acid corresponds to a mixture of strong acid and weak acid, but at a higher temperature when the acid corresponds solely to a weak acid. By way of example, when the weak acid is acetic acid, the reaction temperature will be about 117° C.-118° C.

The starting compound of formula II may be obtained according to the following reaction scheme:

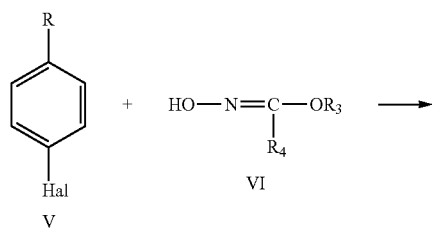

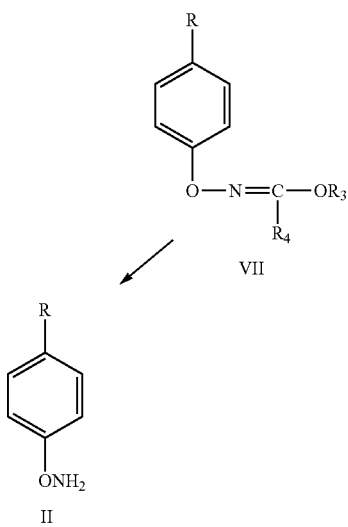

i.e. starting with a halobenzene of formula V in which R represents a nitro or —COOR' group and Hal represents a halogen, for example chlorine or fluorine, which is reacted in the presence of a basic agent such as an alkali metal hydroxide or an alkali metal alkoxide such as sodium tert-butoxide or potassium tert-butoxide, in particular potassium tert-butoxide, with an imidate of formula VI in which $R_3$ represents a linear or branched $C_1$-$C_4$ alkyl group, for example ethyl, and $R_4$ represents a linear or branched $C_1$-$C_4$ alkyl group, for instance methyl, the reaction preceding at room temperature and preferably in a polar solvent such as N,N-dimethylformamide to form an oxime of formula VII in which $R_3$ and $R_4$ have the same meaning as previously. This oxime is then treated with a strong acid such as hydrochloric acid to form the compound of formula II in the form of an acid-addition salt, which is then optionally subjected to the action of a strong base such as sodium hydroxide, to obtain the compound of formula II in free base form.

According to one embodiment, the starting compound of formula II' may be obtained according to the following reaction scheme:

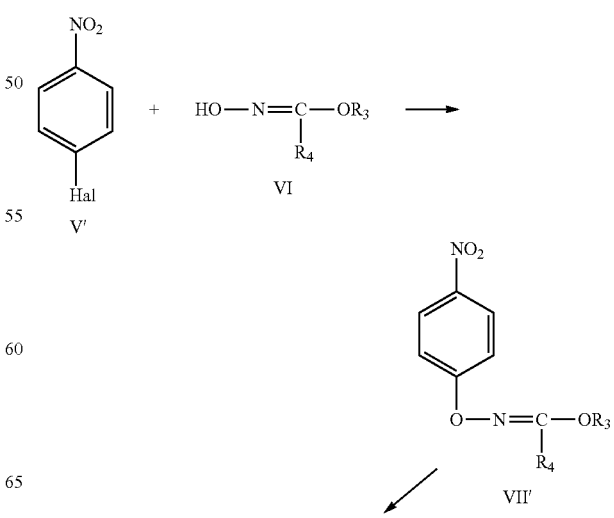

-continued

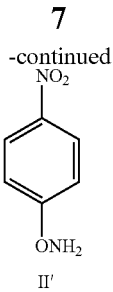
II' i.e. starting with a halonitrobenzene of formula V' in which Hal represents a halogen, for example chlorine, this compound of formula V' corresponding to a compound of formula V in which R represents —$NO_2$, which is reacted in the presence of a basic agent such as an alkali metal hydroxide, with an imidate of formula VI in which $R_3$ represents a linear or branched $C_1$-$C_4$ alkyl group, for example ethyl, and $R_4$ represents a linear or branched $C_1$-$C_4$ alkyl group, for instance methyl, the reaction proceeding at room temperature and, preferably, in a polar solvent such as N,N-dimethylformamide to form an oxime of formula VII' in which $R_3$ and $R_4$ have the same meaning as previously, this compound of formula VII' corresponding to a compound of formula VII in which R represents a nitro group. This oxime is then treated with a strong acid such as hydrochloric acid to form the compound of formula II' in the form of an acid-addition salt, which is then subjected to the action of a strong base such as sodium hydroxide, to obtain the compound of formula II' in free base form.

The starting compound of formula II" may be obtained according to the following reaction scheme:

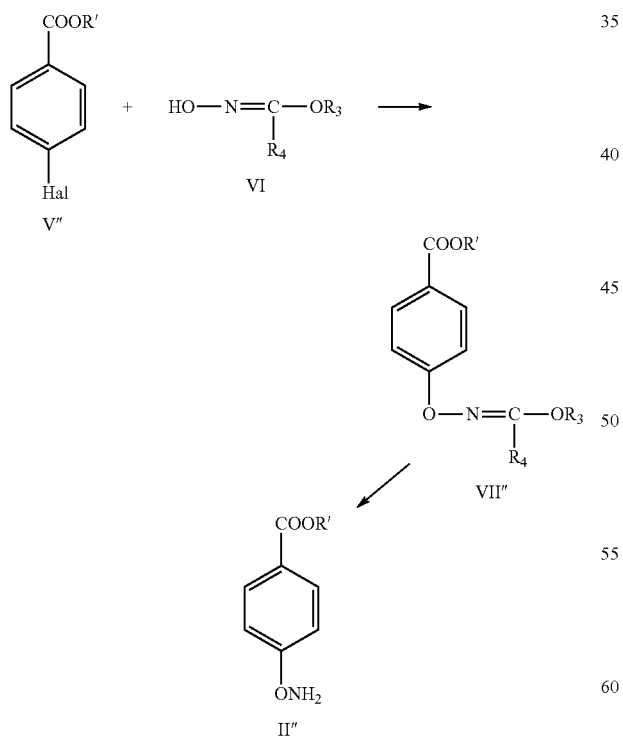

i.e. starting with a halobenzene of formula V" in which Hal represents a halogen, for example chlorine or fluorine, this compound of formula V" corresponding to a compound of formula V in which R represents a group —COOR', R' being as defined previously, which is reacted in the presence of a basic agent such as an alkali metal alkoxide such as sodium tert-butoxide or potassium tert-butoxide, with an imidate of formula VI in which $R_3$ represents a linear or branched $C_{1\text{-}C4}$ alkyl group, for example ethyl, and $R_4$ represents a linear or branched $C_1$-$C_4$ alkyl group, for instance methyl, the reaction proceeding at room temperature and, preferably, in a polar solvent such as N,N-dimethylformamide to form an oxime of formula VII" in which $R_3$ and $R_4$ have the same meaning as previously, this compound of formula VII" corresponding to a compound of formula VII in which R represents a group —COOR', R' being as defined previously. This oxime is then treated with a strong acid such as hydrochloric acid to form the compound of formula II in the form of an acid-addition salt, which is then optionally subjected to the action of a strong base such as sodium hydroxide, to obtain the compound of formula II" in free base form.

As regards the starting diketones of formula III, they may be prepared in various ways according to their chemical structure.

Thus, according to one embodiment, the compounds of formula III' in which $R_1$ has the same meaning as previously and $R_2$ represents an alkoxy or dialkylaminoalkoxy group are referred to hereinbelow as compounds of formula XII. They may be obtained according to the following reaction scheme:

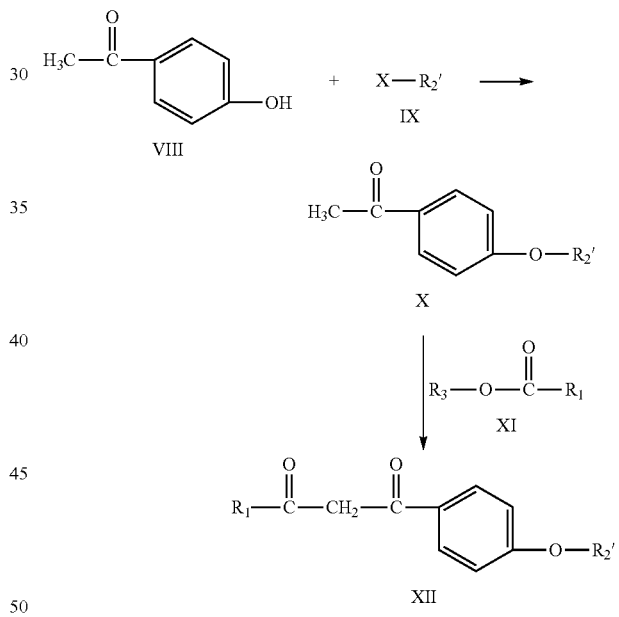

i.e. by reacting 4-hydroxyacetophenone of formula VIII with a halide of formula IX in which $R_2'$ represents an alkyl or dialkylaminoalkyl group and X represents a halogen such as chlorine or a sulfonate group, in the presence of a basic agent, generally a weak base such as an alkali metal carbonate and usually by heating in a polar solvent such as methyl ethyl ketone to give the acetophenone derivatives of formula X in which $R_2'$ has the same meaning as previously.

Preferably, $R_2'$ represents a linear or branched $C_1$-$C_8$ alkyl group, especially a linear or branched $C_1$-$C_4$ alkyl group such as methyl, ethyl, n-propyl, isopropyl, n-butyl, sec-butyl or tert-butyl or alternatively $R_2'$ represents a dialkylaminoalkyl group in which each linear or branched alkyl group is of $C_1$-$C_8$, especially in which each linear or branched alkyl group is of $C_1$-$C_4$ such as methyl, ethyl, n-propyl, isopropyl, n-butyl, sec-butyl or tert-butyl.

The compound of formula X is then coupled with an ester of formula XI in which $R_1$ and $R_3$ have the same meaning as previously, the coupling taking place in the presence of a strong base such as an alkali metal alkoxide and usually in a polar solvent, for example N-methyl-2-pyrrolidinone, to form a diketone of formula XII.

The diketone thus obtained is then isolated directly from the medium in which it is formed or, preferably, after treatment with a strong acid such as hydrochloric acid so as to form an acid-addition salt thereof, for example the hydrochloride. If necessary, this diketone of formula XII in free base form may be regenerated from the acid-addition salt thus obtained, by treating this salt with a basic agent, for example a weak base such as an alkali metal carbonate or hydrogen carbonate.

According to another embodiment, the compounds of formula III'' in which $R_1$ has the same meaning as previously and $R_2$ represents an alkoxy or dialkylaminoalkoxy group are referred to hereinbelow as compounds of formula XII'. They may be obtained according to the following reaction scheme:

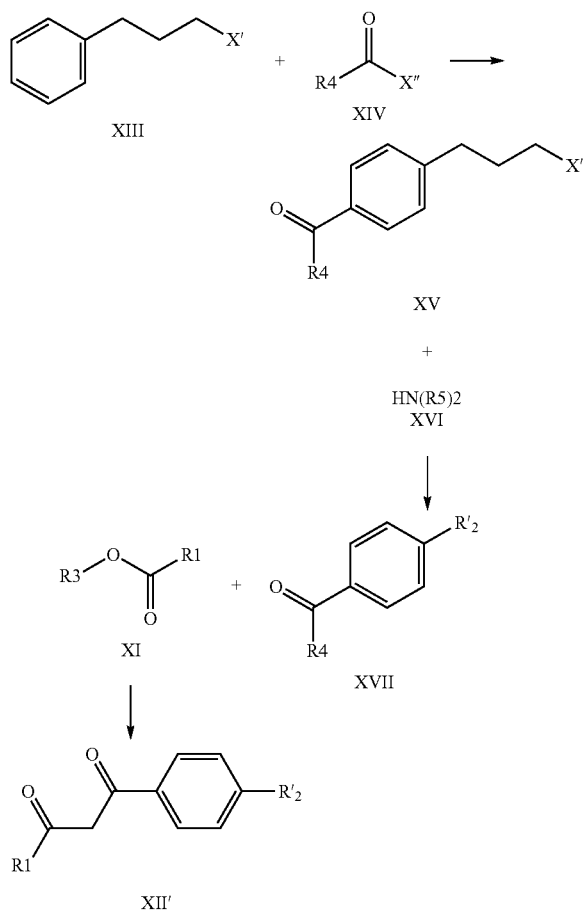

i.e. by reacting a compound of formula XIII in which X' represents a halogen such as chlorine with a halide of formula XIV in which $R_4$ is an alkyl group, especially a $C_1$-$C_4$ alkyl group such as a methyl group and X'' represents a halogen such as chlorine, in the presence of a Lewis acid such as aluminum trichloride or iron trichloride at room temperature in an organic solvent such as dichloromethane to give the compounds of formula XV in which $R_4$ has the same meaning as previously.

The compound of formula XV is then coupled with an amine of formula XVI in which $R_5$ is an alkyl group, especially a $C_1$-$C_4$ alkyl group such as n-butyl, in the presence of an iodide such as potassium iodide or sodium iodide dissolved in a polar aprotic solvent such as methyl isobutyl ketone (MIBK) to give a compound of formula XVII in which $R'_2$ represents a dialkylaminoalkyl group in which the alkyl group represents a $C_1$-$C_4$ alkyl group such as an n-butyl group.

The compound of formula XVII is then coupled with an ester of formula XI in which $R_1$ and $R_3$ have the same meaning as previously, the coupling taking place in the presence of a strong base such as an alkali metal alkoxide and usually in a polar solvent such as N-methyl-2-pyrrolidinone to form a ketone of formula XII'.

The diketone thus obtained is then isolated directly from the medium in which it is formed or, preferably, after treatment with a strong acid such as hydrochloric acid so as to form an acid-addition salt thereof, for example the hydrochloride. If necessary, this diketone of formula XII in free base form may be regenerated from the acid-addition salt thus obtained, by treating this salt with a basic agent, for example a weak base such as an alkali metal carbonate or hydrogen carbonate.

Another subject of the invention relates to the derivatives of general formula:

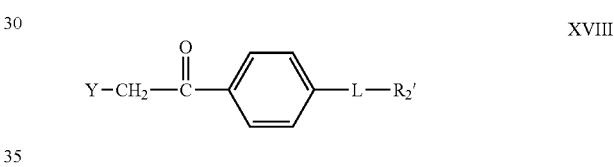

and also to the acid-addition salts thereof, in which $R_2'$ has the same meaning as previously, L represents a bond or an oxygen atom and Y represents:

a) a group of general formula:

in which $R_1'$ represents a $C_1$-$C_4$ alkyl group, or b) a group of general formula:

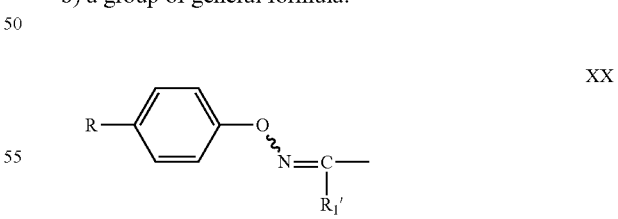

in which $R_1'$ has the same meaning as previously and R represents a nitro or —COOR' group, R' having the same meaning as previously, these derivatives being, when Y represents the group XX, in the form of the E isomer, the Z isomer or mixtures of these isomers.

Another subject of the invention relates to compounds of formula XVIII, referred to hereinbelow as benzoyloxy derivatives of general formula XVIII':

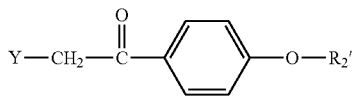
XVIII' and also to the acid-addition salts thereof, in which $R_2'$ has the same meaning as previously and Y represents:
a) a group of general formula:

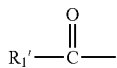
XIX in which $R_1'$ represents a $C_1$-$C_4$ alkyl group, or
b) a group of general formula:

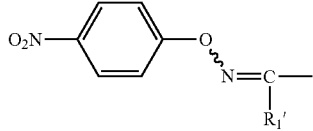
XX' in which $R_1'$ has the same meaning as previously, these benzoyloxy derivatives being, when Y represents the group XX', in the form of the E isomer, the Z isomer or mixtures of these isomers, this group of formula XX' corresponding to a compound of formula XX in which R represents a nitro group.

Another subject of the invention relates to compounds of formula XVIII, referred to hereinbelow as derivatives of general formula XVIII":

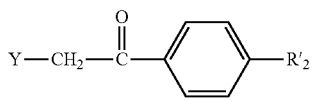
XVIII"

and also to the acid-addition salts thereof, in which $R_2'$ has the same meaning as previously and Y represents:
a) a group of general formula:

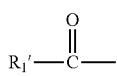
XIX in which $R_1'$ represents a $C_1$-$C_4$ alkyl group, or
b) a group of general formula:

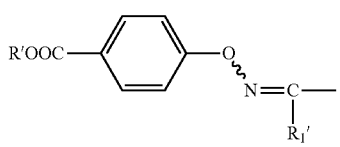
XX"

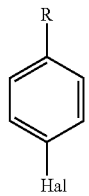
V in which $R_1'$ and R' have the same meaning as previously, these derivatives being, when Y represents the group XX", in the form of the E isomer, the Z isomer or mixtures of these isomers, this compound corresponding to a compound of formula XX in which R represents a group —COOR', R' being as defined previously.

Among the compounds of formula XVIII, those in which Y represents the group of formula XIX or the group of formula XX in which $R_1'$ represents n-butyl constitute preferred compounds.

Moreover, the compounds of formula XVIII in which $R_2'$ represents 3-(di-n-butylamino)propyl also form preferred compounds.

Moreover, the compounds of formula XVIII in which L represents a bond also form preferred compounds.

Moreover, the compounds of formula XVIII in which L represents an oxygen atom also form preferred compounds.

Consequently, compounds of the invention that are particularly preferred are represented by the benzoyloxy derivatives of formula XVIII in which:
a) $R_2'$ represents 3-(di-n-butylamino)propyl, L represents a bond and Y represents the group of formula XIX in which $R_1'$ represents n-butyl,
b) $R_2'$ represents 3-(di-n-butylamino)propyl, L represents a bond and Y represents the group of formula XX in which $R_1'$ represents n-butyl, this compound being in the form of the E isomer, the Z isomer or a mixture of these isomers.

Consequently, compounds of the invention that are particularly preferred are represented by the benzoyloxy derivatives of formula XVIII in which:
a) $R_2'$ represents 3-(di-n-butylamino)propyl, L represents an oxygen atom and Y represents the group of formula XIX in which $R_1'$ represents n-butyl,
b) $R_2'$ represents 3-(di-n-butylamino)propyl, L represents an oxygen atom and Y represents the group of formula XX in which $R_1'$ represents n-butyl, this compound being in the form of the E isomer, the Z isomer or a mixture of these isomers.

Among the compounds of formula XVIII', those in which Y represents the group of formula XIX or the group of formula XX' in which $R_1'$ represents n-butyl constitute preferred compounds.

Moreover, the compounds of formula XVIII' in which $R_2'$ represents 3-(di-n-butylamino)propyl also form preferred compounds.

Consequently, compounds of the invention that are particularly preferred are represented by the benzoyloxy derivatives of formula XVIII' in which:
a) $R_2'$ represents 3-(di-n-butylamino)propyl and Y represents the group of formula XIX in which $R_1'$ represents n-butyl,
b) $R_2'$ represents 3-(di-n-butylamino)propyl and Y represents the group of formula XX' in which $R_1'$ represents n-butyl, this compound being in the form of the E isomer, the Z isomer or a mixture of these isomers.

Consequently, compounds of the invention that are particularly preferred are represented by the benzoyloxy derivatives of formula XVIII' in which:
  a) $R_2'$ represents 3-(di-n-butylamino)propyl and Y represents the group of formula XIX in which $R_1'$ represents n-butyl,
  b) $R_2'$ represents 3-(di-n-butylamino)propyl and Y represents the group of formula XX' in which $R_1'$ represents n-butyl, this compound being in the form of the E isomer, the Z isomer or a mixture of these isomers.

Among the compounds of formula XVIII", those in which Y represents the group of formula XIX or the group of formula XX" in which $R_1'$ represents n-butyl constitute preferred compounds.

Moreover, the compounds of formula XVIII" in which $R_2'$ represents 3-(di-n-butylamino)propyl also form preferred compounds.

Consequently, compounds of the invention that are particularly preferred are represented by the derivatives of formula XVIII" in which:
  a) $R_2'$ represents 3-(di-n-butylamino)propyl and Y represents the group of formula XIX in which $R_1'$ represents n-butyl,
  b) $R_2'$ represents 3-(di-n-butylamino)propyl and Y represents the group of formula XX" in which $R_1'$ represents n-butyl, this compound being in the form of the E isomer, the Z isomer or a mixture of these isomers.

Consequently, compounds of the invention that are particularly preferred are the benzoyloxy derivatives of formula XVIII" in which:
  a) $R_2'$ represents 3-(di-n-butylamino)propyl and Y represents the group of formula XIX in which $R_1'$ represents n-butyl,
  b) $R_2'$ represents 3-(di-n-butylamino)propyl and Y represents the group of formula XX" in which $R_1'$ represents n-butyl, this compound being in the form of the E isomer, the Z isomer or a mixture of these isomers.

The non-limiting examples that follow illustrate the invention. In these examples, the abbreviations below have the indicated meanings:
TLC: thin-layer chromatography
HPLC: high-performance liquid chromatography
LC method used for the analysis of the preparations 2:

| Column: | Symmetry C18 (3.9 × 150 – 5 μm) | | |
|---|---|---|---|
| Eluents: | Route A: Water + 0.1% TFA | | |
| | Route B: Acetonitrile | | |
| Flow rate: | 0.9 mL/minute | | |
| Gradient: | T (min) | Route A (%) | Route B (%) |
| | 0 | 80 | 20 |
| | 20 | 60 | 40 |
| | 35 | 40 | 60 |
| | 37 | 80 | 20 |
| | 47 | 80 | 20 |

UV detection at: λ = 230 nm/260 nm
Temperature: 40° C.

PREPARATIONS 1

I. O-(4-Nitrophenyl)hydroxylamine (Compound II)

A. Ethyl 4-Nitrophenoxyethaneimidoate (Compound VII: $R_3$=$C_2H_5$; $R_4$=$CH_3$)

To a suspension of 23.8 g (0.42 mol) of potassium hydroxide in 220 ml of N,N-dimethylformamide at 10° C. are added 40.0 g of ethyl N-hydroxyethaneimidoate (0.39 mol) (compound VI: $R_3$=$C_2H_5$; $R_4$=$CH_3$). A solution of 55.6 g of 4-chloronitrobenzene (0.35 mol) (compound V: Hal=Cl) (55.6 g) in N,N-dimethylformamide is then added slowly, at 10° C. The mixture is stirred for 24 hours at 20° C. and 1 L of water is then added. The precipitate is filtered off and the solid is washed with water and oven-dried at 30° C. under vacuum to constant weight.
Mass obtained: 72 g
Yield: 91 w/w %

B. O-(4-Nitrophenyl)hydroxylamine (Compound II)

To a solution of 71.2 g of ethyl 4-nitrophenoxyethaneimidoate (0.32 mol) (compound VII) in 925 ml of acetonitrile are added slowly, at 20° C., 35 ml of 37% hydrochloric acid (0.38 mol). The reaction medium is stirred at 20° C. for 2 hours and then filtered, and the O-(4-nitrophenyl)hydroxylamine hydrochloride thus formed is dried at 30° C. in a vacuum oven. With stirring, this hydrochloride is dissolved in a mixture formed from 800 ml of dichloromethane and of a sodium hydroxide solution (16.8 g in 500 ml) and the phases are then allowed to separate by settling. The organic phase is separated out and washed with 500 ml of water. This organic phase is evaporated on a rotary evaporator and the solid obtained is then dried in a vacuum oven.
Mass obtained: 45.5 g
Yield: 93 w/w %

II. 1-{4-[3-(Di-n-butylamino)propoxy]benzoyl}-1,3-heptane-dione (Compound III: $R_1$=n-$C_4H_9$; $R_2$=3-(di-n-butylamino)propoxy)

A. 1-Chloro-3-(di-n-butylamino)propane (Compound IX: $R_2'$=3-(di-n-butylamino)propyl; X=Cl)

70.8 ml of 20% aqueous ammonia solution and then 138.8 ml of a 68.4% solution of 1-chloro-3-(di-n-butylamino)propane hydrochloride (403.9 mmol) are placed in a reactor at room temperature (20-25° C.). The mixture is rinsed with water and then stirred for 15 minutes at 20-25° C., after which the phases are allowed to separate by settling. The aqueous phase is removed and the organic phase is washed with water. After stirring for 15 minutes, the phases are allowed to separate by settling and the aqueous phase is removed. The organic phase thus obtained contains, in crude form, the desired compound IX, which is stored at 5° C. under nitrogen.

B. 4-[3-(Di-n-butylamino)propoxy]acetophenone (Compound X: $R_2'$=3-(di-n-butylamino)propyl)

47.9 g of 4-hydroxyacetophenone (compound VIII) (351.8 mmol) are placed in a reactor and 220 ml of methyl ethyl ketone (4.61 volumes) are added. The mixture is stirred until dissolution is complete, 53.5 g of potassium carbonate (387 mmol) are added and the suspension is stirred again. It is heated to reflux, 1-chloro-3-(di-n-butylamino)propane (compound IX) in free base form is added slowly and the addition funnel is rinsed with methyl ethyl ketone. Refluxing is continued overnight. When the reaction is complete, the mixture is cooled to room temperature and the methyl ethyl ketone is distilled off. The reaction medium is cooled to 25° C. and 200 ml of water are then added. 200 ml of methyl tert-butyl ether are added, the phases are allowed to separate by settling and are separated to give a first aqueous phase and a first organic phase. This aqueous phase and a first organic phase are extracted. This aqueous phase is then extracted with methyl tert-butyl ether, to give a second organic phase. The organic phases are combined and washed with a mixture formed from 200 ml of water, 2.24 ml of 90% acetic acid and 3.75 g of sodium chloride and then twice with aqueous sodium chloride solution. The organic phase is then brought to dryness to obtain the desired compound X.

Mass obtained: 108.4 g

Appearance: very slightly viscous yellow oil a) eluent: 90/10 dichloromethane/methanol
   Rf=0.48 b) eluent: 95/0.5 dichloromethane/methanol
   Rf=0.34

Yield: 100.8 w/w %

C. 1-{4-[3-(Di-n-butylamino)propoxy]phenyl}-1,3-heptanedione hydrochloride (hydrochloride of Compound XII: $R_1$=n-$C_4H_9$; $R_2'$=3-(di-n-butylamino)propyl)

108.4 g of 4-(di-n-butylaminopropoxy)acetophenone (compound X) (355 mmol), 58.1 ml of ethyl pentanoate (39 mmol) and 325 ml of N-methyl-2-pyrrolidinone are placed in a reactor. The mixture is stirred and cooled to 5° C., followed by portionwise addition of 57.5 g of sodium methoxide (1.064 mmol; 3 equivalents). The reaction medium is then allowed to warm to room temperature with continued stirring, which gives compound XII in free base form.

105 g of 37% hydrochloric acid solution are placed in a 1L Keller flask. The solution is cooled to 5° C. and the preceding reaction mixture is added slowly to the hydrochloric acid solution while controlling the exothermicity. At the end of the addition, the reaction medium is transferred into two 1L conical flasks. It is extracted with water and ethyl acetate, twice more with ethyl acetate and then again twice with ethyl acetate. The combined organic phases are washed twice with 150 ml of water. The organic phase is dried, 300 ml of methylcyclohexane are added and the resulting mixture is stirred until a suspension is obtained. It is filtered and the product is rinsed with methylcyclohexane and dried under vacuum at 40° C. to obtain the hydrochloride of the desired compound XII.

Mass obtained: 121.8 g

Appearance: cream-colored solid a) TLC (eluent: 90/10 dichloromethane/methanol)
   Rf: 0.52 b) HPLC
   Rt: 16.0 minutes

Yield: 80.6 w/w %.

D. 1-{4-[3-(Di-n-butylamino)propoxy]phenyl}-1,3-heptanedione (Compound XII: $R_1$=n-$C_4H_9$; $R_2'$=3-(di-n-butylamino)propyl)

To 19.6 g of 1-{4-[3-(di-n-butylamino)propoxy]phenyl}-1,3-heptane-dione hydrochloride, obtained after the extraction described in the preceding paragraph, are added 40 ml of sodium bicarbonate (10 w/w % and 20 ml of water). The mixture is extracted with twice 30 ml of dichloromethane and the organic phases are washed with 60 ml of water. The resulting organic phase is dried over sodium sulfate and evaporated to dryness under vacuum on a rotary evaporator to recover 16.7 g of an orange-colored oil.

EXAMPLE 1

2-n-Butyl-3-{4-[3-(di-n-butylamino)propoxy]benzoyl}-5-nitrobenzofuran (Compound I: $R_1$=n-$C_4H_9$; $R_2$=3-(di-n-butylamino)propoxy)

7.11 g of 1-{4-[3-(di-n-butylamino)propoxy]phenyl}-1,3-heptanedione (compound XII or III) (optical purity: 95%; 17 mmol), 2.81 g of O-(4-nitrophenyl)hydroxylamine (compound II) (18 mmol) and 34 ml of acetic acid are placed in a 100 ml Keller flask. The mixture is stirred at room temperature for 12 hours (formation of the oxime of formula IV: $R_1$=n-$C_4H_9$; $R_2$=3-(di-n-butylamino)propoxy) and is then refluxed (117° C.) for 6 hours. The reaction medium is evaporated to dryness on a rotary evaporator and the crude reaction product is diluted with 60 ml of ethyl acetate. The resulting solution is then hydrolyzed by addition of 100 ml of basic sodium carbonate solution (20 w/w %), the phases are separated by settling and the organic phase is washed with three times 100 ml of water to neutral pH. The organic phase is dried over sodium sulfate, the suspension is filtered and the solvent is evaporated off to dryness using a rotary evaporator.

Mass obtained: 9.01 g

Appearance: colored oil

Titer of the crude product by TLC: 67%

Chemical yield: 69%

PREPARATIONS 2

I. 2-Propyl 4-(aminoxy)benzoate

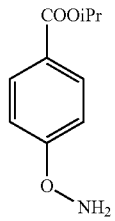

A. 2-Propyl 4-fluorobenzoate

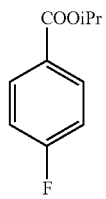

25 g of 4-fluorobenzoic acid are placed in 150 mL of iPA in a reactor, the suspension is then heated to 75° C. and 691 µL of DMF are added. 14.9 mL (24.4 g) of thionyl chloride $SOCl_2$ are added. The reaction mixture is refluxed overnight and the mixture is then concentrated, followed by addition of 100 mL of 5% aqueous ammonia solution and 100 mL of DCM. The organic DCM phase is washed again with water and the pH is adjusted to 7 by addition of dilute hydrochloric acid solution. 31 g of a golden yellow liquid are obtained.

Mass yield =95%

LC: Rt=19.9 minutes

B. 2-Propyl 4-({[(1Z)-1-ethoxyethylidene]amino}oxy)benzoate

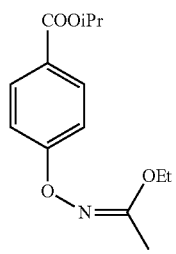

6.1 g of N-hydroxyethaneimidoate in 50 mL of DMF are placed in a reactor and are then cooled to 0° C., followed by addition of 6.7 g of t-BuOK. The mixture is warmed to room temperature and stirred for 30 minutes, followed by addition of 10 g of the product obtained in the preceding step. The reaction mixture is stirred for 2 hours at room temperature, followed by addition of 100 mL of water and 50 mL of DCM. The organic phase is washed with brine and then concentrated to obtain 22.2 g of a golden yellow liquid.

Yield=84%

LC: Rt=24.9 minutes

C. 2-Propyl 4-(aminoxy)benzoate 17 g of the concentrated product obtained in the preceding step (i.e. about 14 g of estimated pure product), 30 mL of dioxane and 11.7 g of 36% hydrochloric acid solution are placed in a round-bottomed flask. The reaction progress is monitored by liquid chromatography. At the end of the reaction, the reaction mixture is filtered through a Büchner funnel and then washed with 5 mL of dioxane. The filtrate is concentrated under vacuum on a rotavapor; the yellow precipitate is taken up in 20 mL of iPA and dissolved while hot. After cooling to room temperature, isopropyl ether is added and the crystals formed are then filtered off: 0.4 g of expected product is isolated. A second crystallization crop from methylcyclohexane (MCH) makes it possible to recover a further 11.5 g.

Yield =95%

LC: Rt=14.8 minutes

II. 1-{4-[3-(Dibutylamino)propyl]phenyl}heptane-1,3-dione

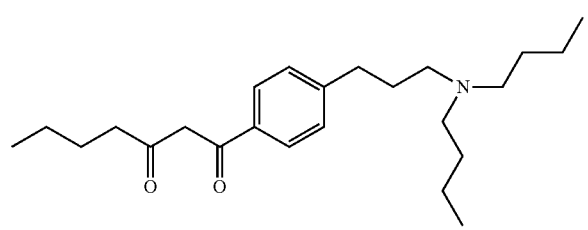 [SMILES: CCCCC(=O)CC(=O)c1ccc(CCCN(CCCC)CCCC)cc1]

A. 1-[4-(3-chloropropyl)phenyl]ethanone

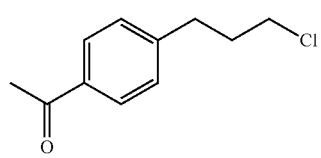

84 mL of CH$_2$Cl$_2$ and 14.4 g (1.1 eq.) of aluminum trichloride (AlCl$_3$) are placed in a reactor at 20° C. with stirring. The reaction medium is cooled to −7° C. and 8.5 g (1.1 eq.) of acetyl chloride are then added. The mixture is stirred for 30 minutes and 15 g of 1-chloro-3-phenylpropane are then added at 0° C. At the end of the reaction, the reaction mixture is poured over about 30 minutes with vigorous stirring into 75 mL of 5% hydrochloric acid solution. The mixture is stirred for 1 hour at 10° C., the phases are then separated by settling and the aqueous phase is extracted with CH$_2$Cl$_2$. The organic phases are combined and washed successively with 2N HCl solution, 1N sodium hydroxide solution and water.

The organic phase is dried over Na$_2$SO$_4$ and then filtered. After evaporating to dryness, 19.9 g of a yellow oil are obtained.

Quantitative yield

LC: Rt=18 minutes

B. 1-{4-[3-(dibutylamino)propyl]phenyl}ethanone

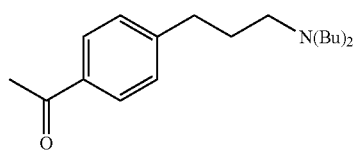

20.5 g of the product obtained in the preceding step and 100 mL of MIBK are placed in a reactor. This solution is stripped with about 50 ml of MIBK under vacuum (60° C./100 mbar). The solution is then adjusted to 130 g by adding MIBK. To this solution are added 2.7 g of sodium iodide with vigorous stirring, followed by addition over 10 minutes, at about 20° C., of 31 g (2.5 eq.) of dibutylamine. The reaction medium is refluxed with vigorous stirring for 14 hours. The reaction mixture is cooled to 20° C. and hydrolyzed with water. The organic phase is successively washed with water, hydrochloric acid solution, water, aqueous potassium carbonate solution and aqueous sodium chloride solution. The aqueous phases are treated with sodium hydroxide and back-extracted with dichloromethane. The organic phases are combined to give, after concentrating to dryness, 20.6 g of a brown oil.

Yield=74%

LC: Rt=10.5 minutes

C. 1-{4-[3-(Dibutylamino)propyl]phenyl}heptane-1,3-dione 10 g of the product obtained in the preceding step, 5 g of ethyl pentanoate and 30 mL of NMP are placed in a reactor. 5.6 g of sodium methoxide are added, at 5° C. The mixture is warmed to room temperature and the reaction progress is monitored by thin-layer chromatography. At the end of the reaction, the reaction medium is poured into a mixture of 10.1 g of 37% hydrochloric acid solution, 45 g of water and 45 g of ice. The product is then extracted with twice 50 mL of heptane and the combined organic phases are washed with 100 mL of water. The organic phases are washed with aqueous sodium bicarbonate solution. The organic phase is concentrated to give 10.6 g of a carmine-red liquid.

Yield=82%

LC: Rt=14.3 and 17 minutes

The two main peaks on LC at Rt=14.3 minutes and Rt=17 minutes correspond to the expected product in ketone and enol form.

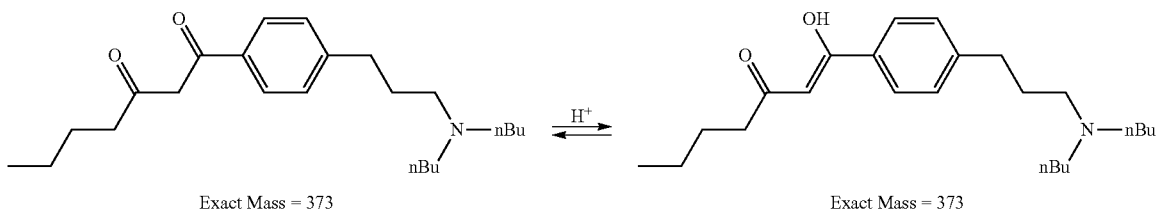

Structure confirmed by mass spectrometry analysis (M+H=374 i.e. MW=373).

EXAMPLE 2

Synthesis of Celivarone

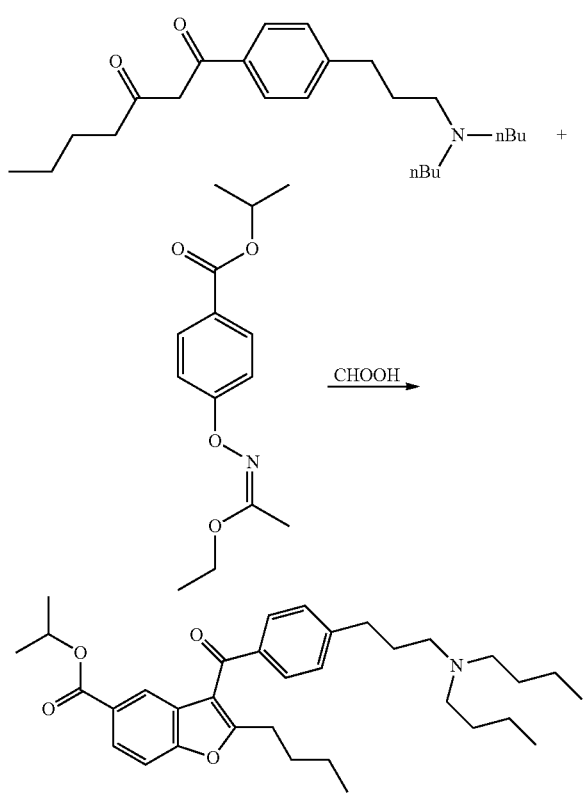

2.16 g of 2-propyl 4-({[(1Z)-1-ethoxyethylidene]amino}oxy)benzoate, 6 ml of formic acid and 2 g of 1-{4-[3-(dibutylamino)propyl]phenyl}heptane-1,3-dione are placed in a reactor.

890 μL of HCl (37%) are added and the reaction medium is heated at 50° C. for 2 hours (the end of reaction is monitored by LC). The medium is hydrolyzed by adding 20 mL of aqueous sodium bicarbonate solution. The mixture is extracted with 25 mL of DCM and the DCM phase is then washed with 15 mL of water. After concentrating under vacuum, 3.1 g of crude product are isolated in the form of an oil. The product is purified by chromatography on silica gel, eluting with a DCM/iPA mixture, and 1.1 g of celivarone base are recovered in oil form in the main fraction.

Yield=38%

LC: Rt=20 minutes.

What is claimed is:

1. A process for preparing a benzofuran derivative substituted at position 5 of formula I:

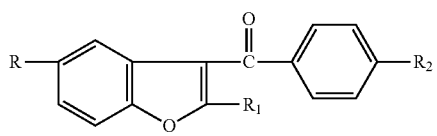

in which R represents a nitro or ester group —COOR', in which R' represents a hydrogen atom or an alkyl group; $R_1$ represents hydrogen or an alkyl group; and $R_2$ represents hydrogen, a halogen, haloalkyl, alkyl, alkoxy, dialkylaminoalkoxy or dialkylaminoalkyl group;

said process comprising coupling a hydroxylamine of formula II:

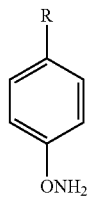

in the presence of an acid, with a diketone of formula III:

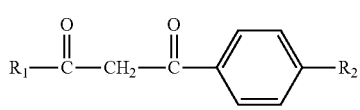

in which $R_1$ and $R_2$ have the same meaning as above, to form an oxime of formula IV:

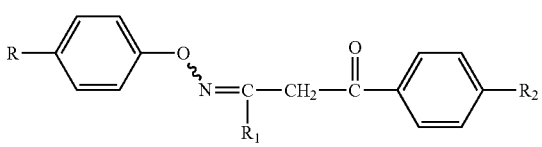

in the form of a mixture of E and Z isomers, in which $R_1$ and $R_2$ have the same meaning as above, and cyclizing this oxime by heating to form the desired compound.

2. The process as claimed in claim 1, in which R represents an ester —COOR' in which R' represents an alkyl group; $R_1$ represents an alkyl group; and $R_2$ represents hydrogen, haloalkyl, dialkylaminoalkoxy or dialkylaminoalkyl group.

3. The process as claimed in claim 1, wherein the acid is a weak acid optionally combined with a strong acid.

4. The process as claimed in claim 3, wherein the weak acid is acetic acid.

5. The process as claimed in claim 1, wherein the oxime is cyclized in the medium in which it is formed.

6. The process as claimed in claim 1, in which:
$R_1$ represents a linear or branched $C_1$-$C_8$ alkyl group; and
$R_2$ represents a linear or branched $C_1$-$C_8$ alkyl group, a linear or branched $C_1$-$C_8$ alkoxy group or a dialkylaminoalkoxy group in which each alkyl group is of $C_1$-$C_8$, and the linear or branched alkoxy group is of $C_1$-$C_8$.

7. The process as claimed in claim 6, in which:
$R_1$ represents a linear or branched $C_1$-$C_4$ alkyl group; and
$R_2$ represents a linear or branched $C_1$-$C_4$ alkyl group, a linear or branched $C_1$-$C_4$ alkoxy group or a dialkylaminoalkoxy group in which each alkyl group is of $C_1$-$C_4$, and the linear or branched alkoxy group is of $C_1$-$C_4$.

8. The process as claimed in claim 6, in which $R_1$ represents n-butyl and $R_2$ represents 3-(di-n-butylamino)propoxy.

9. The process as claimed in claim 6, in which $R_1$ represents n-butyl and $R_2$ represents 3-(di-n-butylamino)propyl.

10. The process as claimed in claim 1, comprising obtaining the compound by reacting a halobenzene of formula V:

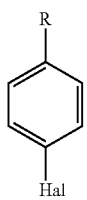

V in which Hal represents a halogen; with an imidate of formula VI:

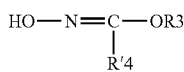

VI in which $R_3$ and $R_4$ each represent a linear or branched $C_1$-$C_4$ alkyl group; the reaction proceeding at room temperature and in a polar solvent, to form an oxime of formula VII:

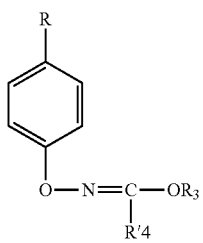

VII in which $R_3$ and $R_4$ have the same meaning as above;
and treating this oxime with a strong acid to form the desired compound of formula II in the form of the acid-addition salt, and then subjecting this salt to the action of a strong base to obtain the compound of formula II in free base form.

11. The process as claimed in claim 1, wherein a diketone of formula III in which $R_1$ represents hydrogen or an alkyl group and $R_2$ represents an alkoxy or diaminoalkoxy group is obtained, said method comprising
a) reacting a 4-hydroxyacetophenone of formula VIII:

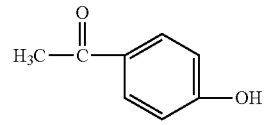

VIII with a halide of formula IX:

IX in which $R_2'$ represents an alkyl or dialkylaminoalkyl group and X represents a halogen or a sulfonate group; in the presence of a basic agent, and heating in a polar solvent to give an acetophenone derivative of formula X:

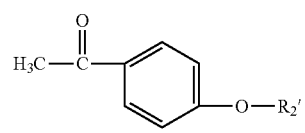

X in which $R_2'$ has the same meaning as above; and
b) coupling the compound of formula X with an ester of formula XI:

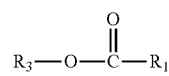

XI in which $R_1$ has the same meaning as above and $R_3$ represents a linear or branched $C_1$-$C_4$ alkyl group; the coupling taking place in the presence of a strong base and in a polar solvent, to form a diketone of formula XII:

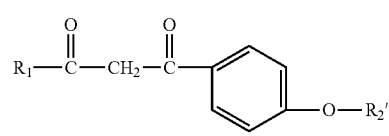

XII in which $R_2$ and $R_2'$ have the same meaning as above, and isolating this diketone directly from the medium in which it is formed or after treatment with a strong acid to form an acid-addition salt thereof.

12. The process as claimed in claim 1, comprising obtaining the compound of formula II'', which is a compound of formula II, by reacting a halobenzene of formula V'':

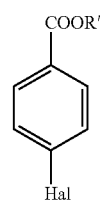

V'' in which Hal represents a halogen, with an imidate of formula VI:

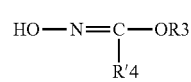

VI in which $R_3$ and $R_4$ each represent a linear or branched $C_1$-$C_4$ alkyl group, the reaction proceeding at room temperature and in a polar solvent, to form an oxime of formula VII":

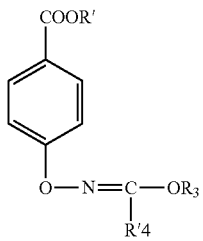

VII"

in which $R_3$ and $R_4$ have the same meaning as above; and treating this oxime with a strong acid to form the desired compound of formula II' in the form of an acid-addition salt thereof, and then subjecting this salt to the action of a strong base to obtain the compound of formula II" in free base form.

13. The process as claimed in claim 1, comprising obtaining the diketone of formula III" in which $R_1$ represents hydrogen or an alkyl group and $R_2$ represents an alkoxy or dialkylaminoalkoxy group; X' and X" represent a halogen and $R_4$ is an alkyl group; comprising:

a) reacting a compound of formula XIII:

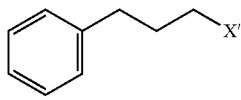

XIII with a compound of formula XIV:

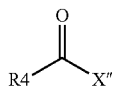

XIV to obtain a compound of formula XV:

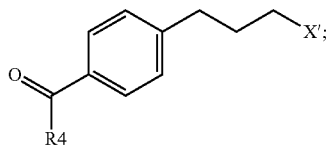

XV and b) reacting said compound of formula XV with a compound of formula XVI: $HN(R_5)_2$ to obtain a compound of formula XVII:

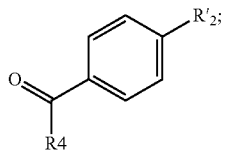

XVII and c) reacting said compound of formula XVII with a compound of formula XI:

XI to obtain the compound of formula III".

14. A benzoyloxy derivative of formula XVIII:

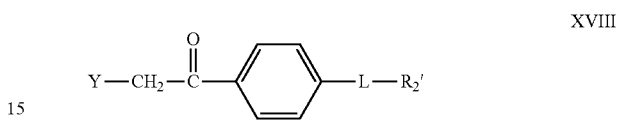

XVIII or an acid-addition salt thereof, in which L represents a bond or an oxygen atom, $R_2'$ represents a linear or branched $C_1$-$C_4$ alkyl group or a dialkylaminoalkyl group in which each linear or branched alkyl group is of $C_1$-$C_4$, and Y represents:

a) a group of formula XIX:

XIX in which $R_1'$ represents a $C_1$-$C_4'$ alkyl group, or b) a group of formula XX:

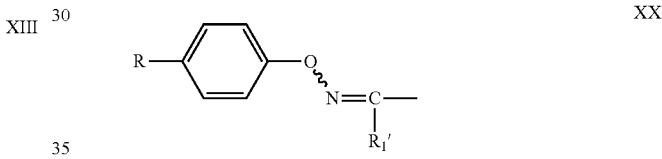

XX in which $R_1'$ has the same meaning as above, these derivatives being, when Y represents a group XX, in the form of the E isomer, the Z isomer or a mixture of these isomers.

15. The benzoyloxy derivative as claimed in claim 14, in which Y represents the group of formula XIX or the group of formula XX in which $R_1'$ represents n-butyl.

16. The benzoyloxy derivative as claimed in claim 14, in which $R_2'$ represents 3-(di-n-butylamino)propyl.

17. The benzoyloxy derivative as claimed in claim 14, in which $R_2'$ represents 3-(di-n-butylamino)propyl, L represents an oxygen atom, and Y represents the group of formula XIX in which $R_1'$ represents n-butyl.

18. The benzoyloxy derivative as claimed in claim 14, in which $R_2'$ represents 3-(di-n-butylamino)propyl, L represents an oxygen atom, and Y represents the group of formula XX in which $R_1'$ represents n-butyl, this compound being in the form of the E isomer, the Z isomer or a mixture of these isomers.

19. The benzoyloxy derivative as claimed in claim 14, in which $R_2'$ represents 3-(di-n-butylamino)propyl, L represents a bond, and Y represents the group of formula XIX in which $R_1'$ represents n-butyl.

20. The benzoyloxy derivative as claimed in claim 14, in which $R_2'$ represents 3-(di-n-butylamino)propyl, L represents a bond, and Y represents the group of formula XX in which $R_1'$ represents n-butyl, this compound being in the form of the E isomer, the Z isomer or a mixture of these isomers.

21. The process according to claim 13 wherein X and X' are chloro.

22. The process according to claim 13 wherein $R_4$ is $C_1$-$C_4$ alkyl.

* * * * *